(12) United States Patent
Xiang

(10) Patent No.: US 10,165,798 B2
(45) Date of Patent: Jan. 1, 2019

(54) METHOD FOR MANUFACTURING ELECTRIC HEATING WIRE ELEMENT

(71) Applicant: HUIZHOU KIMREE TECHNOLOGY CO., LTD, Huizhou, Guangdong (CN)

(72) Inventor: Zhiyong Xiang, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 302 days.

(21) Appl. No.: 15/068,904

(22) Filed: Mar. 14, 2016

(65) Prior Publication Data

US 2016/0192711 A1 Jul. 7, 2016

Related U.S. Application Data

(63) Continuation of application No. PCT/CN2014/089991, filed on Oct. 31, 2014.

(51) Int. Cl.
*A24F 47/00* (2006.01)
*B21F 15/00* (2006.01)
(Continued)

(52) U.S. Cl.
CPC .............. *A24F 47/008* (2013.01); *B21F 3/04* (2013.01); *B21F 15/00* (2013.01); *A61M 11/042* (2014.02); *A61M 2207/10* (2013.01)

(58) Field of Classification Search
CPC .............. A61M 15/016; A61M 11/042; A61M 2207/00; A61M 2207/10; A24F 47/008;
(Continued)

(56) References Cited

U.S. PATENT DOCUMENTS 3,574,931 A * 4/1971 Mochizuki ............. H01C 17/04
228/903
8,857,446 B2 * 10/2014 Wu ....................... A24F 47/008
128/202.21
(Continued)

FOREIGN PATENT DOCUMENTS

CN 103506525 A 1/2014
CN 203424292 U 2/2014
(Continued)

OTHER PUBLICATIONS

"Making an Atomizer Coil 101 (Actual Working Methods Only)", Discussion forum, main author: "Vaporer", Jan. 31, 2010. https://www.e-cigarette-forum.com/threads/making-an-atomizer-coil-101-actual-working-methods-only.65250/.*
(Continued)

*Primary Examiner* — Peter DungBa Vo
*Assistant Examiner* — Jeffrey Carley
(74) *Attorney, Agent, or Firm* — U.S. Fairsky LLP; Yue (Robert) Xu

(57) ABSTRACT

An electric heating wire winding device and a method for manufacturing an electric heating wire element are provided by the present application. The electric heating wire winding device includes a connection assembly, a delivering assembly and a wire winding assembly. The wire winding assembly includes a first clamping component, a second clamping component, a first rotating component, a second rotating component, a first power device, a second power device and a third clamping component. When the electronic wire with the first preset length connected to the free end of the electric heating wire rotates together with the liquid guiding rope and they are moved in an axial direction of the liquid guiding rope away from the first clamping component, the electric heating wire is winded around the liquid guiding rope. The method for manufacturing an electric heating wire element
(Continued)

according to the present application improves the working efficiency.

6 Claims, 8 Drawing Sheets

(51) Int. Cl.
    *B21F 3/04*     (2006.01)
    *A61M 11/04*     (2006.01)

(58) Field of Classification Search
    CPC ...... B21F 3/04; B21F 15/00; Y10T 29/49169; Y10T 29/49174
    See application file for complete search history.

(56) References Cited

U.S. PATENT DOCUMENTS

| | | | | |
|---|---|---|---|---|
| 9,210,738 | B2* | 12/2015 | Ward | H05B 3/00 |
| 9,439,456 | B2* | 9/2016 | Liu | A24F 47/008 |
| 2012/0145169 | A1* | 6/2012 | Wu | A24F 47/008 |
| | | | | 131/273 |
| 2013/0192623 | A1 | 8/2013 | Tucker et al. | |
| 2013/0213419 | A1* | 8/2013 | Tucker | A24F 47/008 |
| | | | | 131/328 |
| 2014/0157583 | A1* | 6/2014 | Ward | H05B 3/00 |
| | | | | 29/611 |
| 2014/0270730 | A1* | 9/2014 | DePiano | A24F 47/008 |
| | | | | 392/404 |

FOREIGN PATENT DOCUMENTS

| | | |
|---|---|---|
| CN | 203523812 U | 4/2014 |
| CN | 203630559 U | 6/2014 |
| CN | 103960784 A | 8/2014 |
| CN | 203872999 U | 10/2014 |
| WO | 2014012907 A1 | 1/2014 |

OTHER PUBLICATIONS

International Search Report for PCT/CN2014/089991, dated Jul. 7, 2015, ISA/CN.

* cited by examiner

METHOD FOR MANUFACTURING ELECTRIC HEATING WIRE ELEMENT

CROSS-REFERENCE TO RELATED APPLICATION

This application is a continuation of International Application No. PCT/CN2014/089991, titled "ELECTRIC HEATING WIRE WINDING DEVICE AND METHOD FOR MANUFACTURING ELECTRIC HEATING WIRE ELEMENT", filed on Oct. 31, 2014, the entire disclose of which is incorporated herein by this reference.

TECHNICAL FIELD

The present application relates to the technical field of electronic cigarettes, and in particular to an electric heating wire winding device and a method for manufacturing an electric heating wire element.

BACKGROUND

An electronic cigarette is a common electronic product that simulates a real cigarette. The electronic cigarette mainly includes an atomizer and a battery pole component. The battery pole component provides electric energy for the atomizer, such that an electric heating wire in the atomizer generates heat to atomize a smoke solution in a liquid guiding rope inside the atomizer so as to release vapor, thereby realizing the effect of simulating a real cigarette.

An electric heating wire element for atomizing tobacco liquid is provided inside the atomizer, and an electric heating wire on the electric heating wire element is generally winded around the liquid guiding rope manually.

The electric heating wire, which is manually winded around the liquid guiding rope, causes a low working efficiency, wastes too much manual labor, and has a large consumption for production cost of a factory. And a length of the manually winded electric heating wire is unable to be accurately controlled, which may adversely affect product quality of the electronic cigarette, and further adversely affects service life and user experience of the electronic cigarette.

SUMMARY

An electric heating wire winding device and a method for manufacturing an electric heating wire element are provided by the present application for winding an electric heating wire around a liquid guiding rope, which improves the working efficiency.

An electric heating wire winding device is provided according to a first aspect of the present application, which includes a connection assembly, a delivering assembly, and a wire winding assembly.

The connection assembly is configured to connect an electronic wire with a first preset length to an electric heating wire in a delivering path, and the electric heating wire includes at least two heating sections for atomizing tobacco liquid and at least one connection section for connecting a power source of an electronic cigarette. The heating sections are spaced apart and are connected via the connection section, and the electronic wire with the first preset length is connected to the connection section of the electric heating wire.

The delivering assembly is connected to the connection assembly for delivering an electric heating wire connected with the electronic wire having the first preset length to the wire winding assembly.

The wire winding assembly includes a first clamping component, a second clamping component, a first rotating component, a second rotating component, a first power device, a second power device, and a third clamping component.

The first clamping component and the second clamping component are oppositely arranged for respectively clamping two ends of a liquid guiding rope. The first rotating component is connected to the first clamping component, the second rotating component is connected to the second clamping component, the first power device is connected to the first rotating component and the second rotating component for driving the first rotating component and the second rotating component, and the second power device is connected to the second clamping component for driving the second power device.

The third clamping component is arranged on the second clamping component and faces to the first clamping component for clamping the electronic wire with the first preset length connected to a free end of the electric heating wire.

The first power device is configured to rotate the first rotating component and the second rotating component, and the second power device is configured to move the second clamping component in an axial direction of the liquid guiding rope.

In the case that the electronic wire with the first preset length connected to the free end of the electric heating wire rotates together with the liquid guiding rope and they move in the axial direction of the liquid guiding rope away from the first clamping component, the electric heating wire is winded around the liquid guiding rope.

Incorporating with the first aspect of the present application, in a first implementing mode of the first aspect of the present application, the wire winding component further includes a cutting component, which includes a first cutting component, a second cutting component, and a third cutting component.

The first cutting component and the second cutting component are both arranged at one end, close to the first clamping component, of the second clamping component, and the third cutting component is arranged at one end, away from the first clamping component, of the second clamping component.

The first cutting component is configured to cut off the electric heating wire at one end, away from the third clamping component, of the electronic wire with the first preset length after the electronic wire with the first preset length connected to the free end of the electronic wire is clamped by the third clamping component.

The second cutting component is configured to cut off the electric heating wire at one end, away from the third clamping component, of another electronic wire with the first preset length adjacent to the electronic wire with the first preset length after the electric heating wire is winded around the liquid guiding rope.

The third cutting component is configured to cut off the liquid guiding rope after the liquid guiding rope winded with the electric heating wire is delivered to the third cutting component, thus a liquid guiding rope with a second preset length is obtained.

Incorporating with the first implementing mode of the first aspect of the present application, in a second implementing mode of the first aspect of the present application, the third cutting component is provided with a fourth clamping component, a fifth clamping component, a cutting tool, a first air cylinder, a second air cylinder and a third air cylinder.

The fourth clamping component and the fifth clamping component are oppositely arranged for respectively clamping two ends of the liquid guiding rope winded with the electric heating wire.

The cutting tool is arranged at an end surface of the fourth clamping component.

The first air cylinder is connected to the cutting tool for pushing the cutting tool to cut off the liquid guiding rope.

The second air cylinder is connected to the fourth clamping component so as to allow the fourth clamping component to clamp or loosen the liquid guiding rope.

The third air cylinder is connected to the fifth clamping component so as to allow the fifth clamping component to clamp or loosen the liquid guiding rope.

Incorporating with the first implementing mode of the first aspect of the present application, in a third implementing mode of the first aspect of the present application, the first cutting component is provided with a cutting tool, a fixing block and a fourth air cylinder.

One end of the fixing block is connected to the cutting tool and is configured to fix the cutting tool.

The fourth air cylinder is connected at another end of the fixing block and configured to push the fixing block and allow the cutting tool to cut off the electric heating wire at one end, away from the third clamping component, of the electronic wire with the first preset length.

Incorporating with the third implementing mode of the first aspect of the present application, in a fourth implementing mode of the first aspect of the present application, the fixing block is provided with a funnel-shaped port.

The funnel-shape port is located at an end portion of the fixing block in contact with the electric heating wire, and is configured to allow the electronic wire with the first preset length having a larger diameter compared with the electric heating wire to be clamped by the funnel-shaped port to be not in contact with the cutting tool, and to allow the electric heating wire having a smaller diameter compared with the electronic wire with the first preset length to fall into the funnel-shaped port to be cut off by the cutting tool.

Incorporating with the first aspect, the first implementing mode of the first aspect, or the second implementing mode of the first aspect of the present application, in a fifth implementing mode of the first aspect of the present application, the third clamping component is provided with a mechanical hand, a clamping piece, a connecting shaft, a fifth air cylinder, a sixth air cylinder and a seventh air cylinder.

The mechanical hand is configured to deliver the electric heating wire connected with the electronic wire with the first preset length to the clamping piece.

The clamping piece is rotatably connected to the connecting shaft.

The fifth air cylinder is connected to the mechanical hand to move the mechanism hand transversely.

The sixth air cylinder is connected to the mechanical hand to move the mechanism hand longitudinally.

The seventh air cylinder is connected to the mechanical hand to fasten or loosen the mechanism hand.

Incorporating with the first aspect, the first implementing mode of the first aspect or the second implementing mode of the first aspect of the present application, in a sixth implementing mode of the first aspect of the present application, the connection assembly is provided with a riveting machine, a wire sending pipe and an airflow source.

The riveting machine is configured to rivet the electric heating wire and the electronic wire with the first preset length.

One end of the wire sending pipe is fixedly arranged at a riveting portion of the riveting machine and is configured to deliver the electronic wire with the first preset length to the riveting portion of the riveting machine.

The airflow source is arranged at another end of the wire sending pipe, and is configured to blow the electronic wire with the first preset length to the riveting portion of the riveting machine from the wire sending pipe.

Incorporating with the first aspect of the present application, in a seventh implementing mode of the first aspect of the present application, the electric heating wire winding device is fixedly provided with a roller for delivering a connecting terminal of the electric heating wire and the electronic wire with the first preset length to the connection assembly.

Incorporating with the first aspect of the present application, in an eighth implementing mode of the first aspect of the present application, the electric heating wire winding device further includes a first tension device and a second tension device.

The first tension device is fixedly arranged at one end of the liquid guiding rope and is connected to the liquid guiding rope, and is configured to control the tension of the liquid guiding rope.

The second tension device is fixedly arranged at one end of the electric heating wire and is connected to the electric heating wire, and is configured to control the tension of the electric heating wire.

Incorporating with the first aspect of the present application, in a ninth implementing mode of the first aspect of the present application, the second clamping component is provided with a clamping piece, multiple springs, and an eighth air cylinder.

The clamping piece is configured to clamp a free end of the liquid guiding rope.

The eighth air cylinder is connected to the clamping piece, and is configured to push the clamping piece to loosen in the case that the second power device allows the second clamping component to move in the axial direction of the liquid guiding rope, thus allowing the liquid guiding rope to be in a loosened state.

The springs are connected to the clamping piece, and are configured to clamp the liquid guiding rope through an elastic potential energy of the springs in the case that the eighth air cylinder returns to an initial state.

A method for manufacturing the electric heating wire element is provided in a second aspect of the present application, and the electric heating wire element includes a liquid guiding rope and an electric heating wire winded around the liquid guiding rope. The method includes:

delivering an electric heating wire towards a first predetermined position, wherein the electric heating wire includes at least two heating sections for atomizing tobacco liquid and at least one connection section for connecting a power source of an electronic cigarette, and the heating sections are spaced apart and are connected via the connection section;

connecting electronic wire with the first preset length to the electric heating wire in the delivering path, wherein the electronic wire with the first preset length connected to the connection section of the electric heating wire;

clamping the electronic wire with the first preset length connected to a free end of the electric heating wire when the electric heating wire reaches the predetermined position; and rotating the electronic wire with the first preset length connected to the free end of the electric heating wire and a pre-clamped liquid guiding rope together and moving them in an axial direction of the liquid guiding rope so as to allow the electric heating wire to be winded around the liquid guiding rope.

Incorporating with the second aspect of the present application, in a first implementing mode of the second aspect of the present application and following the step of clamping the electronic wire with the first preset length connected to a free end of the electric heating wire, the method further includes:

cutting off the connection section at one end away from the first predetermined position of the heating section in the free end of the electric heating wire.

Incorporating with the second aspect or the first implementing mode of the present application, in a second implementing mode of the second aspect of the present application and following the step of winding the electric heating wire around the liquid guiding rope, the method further includes:

cutting off the connection section at one end adjacent to the first predetermined position of the heating section in the free end of the electric heating wire;

delivering the liquid guiding rope winded with the electric heating wire to a second predetermined position; and cutting off the liquid guiding rope to obtain the liquid guiding rope of a second preset length.

Incorporating with the second aspect of the present application, in a third implementing mode of the second aspect of the present application, the step of cutting off the liquid guiding rope specifically includes:

clamping the free end and the connection end of the liquid guiding rope respectively; and cutting off the connection end of the liquid guiding rope to obtain a liquid guiding rope with a second length winded with the electric heating wire.

According to the above technical solutions, the present application has following advantages. The third clamping component is arranged on the second clamping component and faces to the first clamping component for clamping the electronic wire with the first preset length connected to the free end of the electric heating wire; the first power device is configured to rotate the first rotating component and the second rotating component, the second power device is configured to move the second clamping component in the axial direction of the liquid guiding rope; when the electronic wire with the first preset length connected to the free end of the electric heating wire rotates together with the liquid guiding rope and they are moved in the axial direction of the liquid guiding rope away from the first clamping component, the electric heating wire is winded around the liquid guiding rope. Therefore, the wire winding device according to the present application can not only improve the working efficiency, but also accurately control a length of the winded electric heating wire, which ensures the quality and the service life of electronic cigarette products.

DETAILED DESCRIPTION

Figure 1:
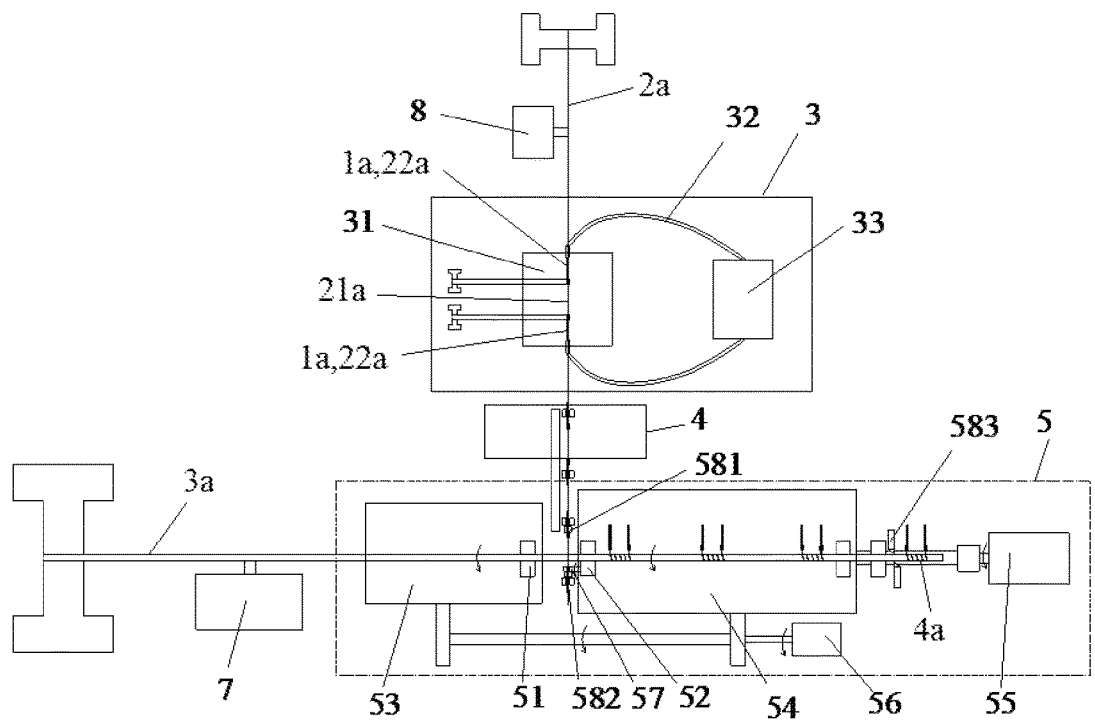
FIG. 1 is a schematic view showing the structure of a preferred embodiment of an electric heating wire winding device according to the present application.
Figure 2:
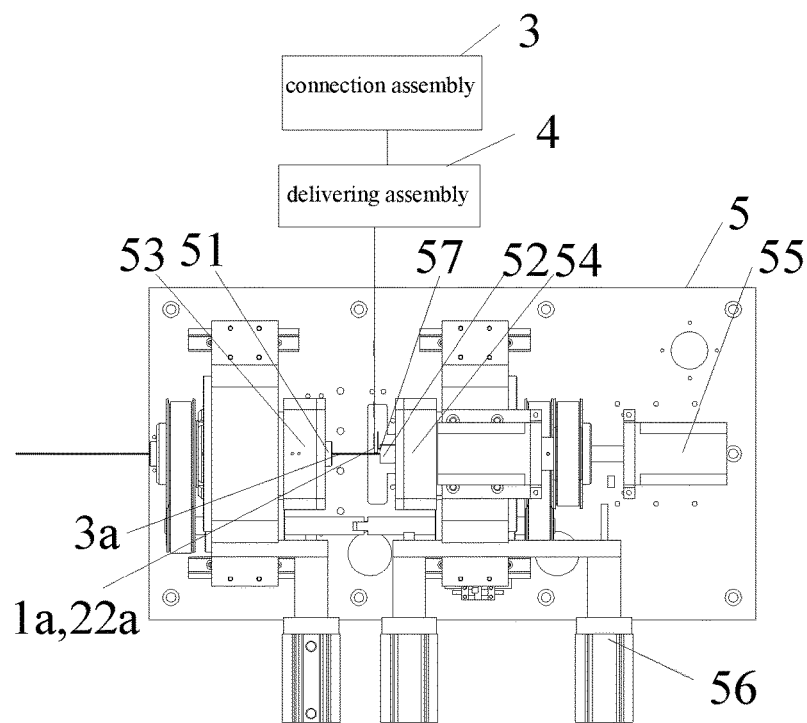
FIG. 2 is a sectional schematic view showing the structure of the preferred embodiment of an electric heating wire winding device according to the present application.
Figure 3:
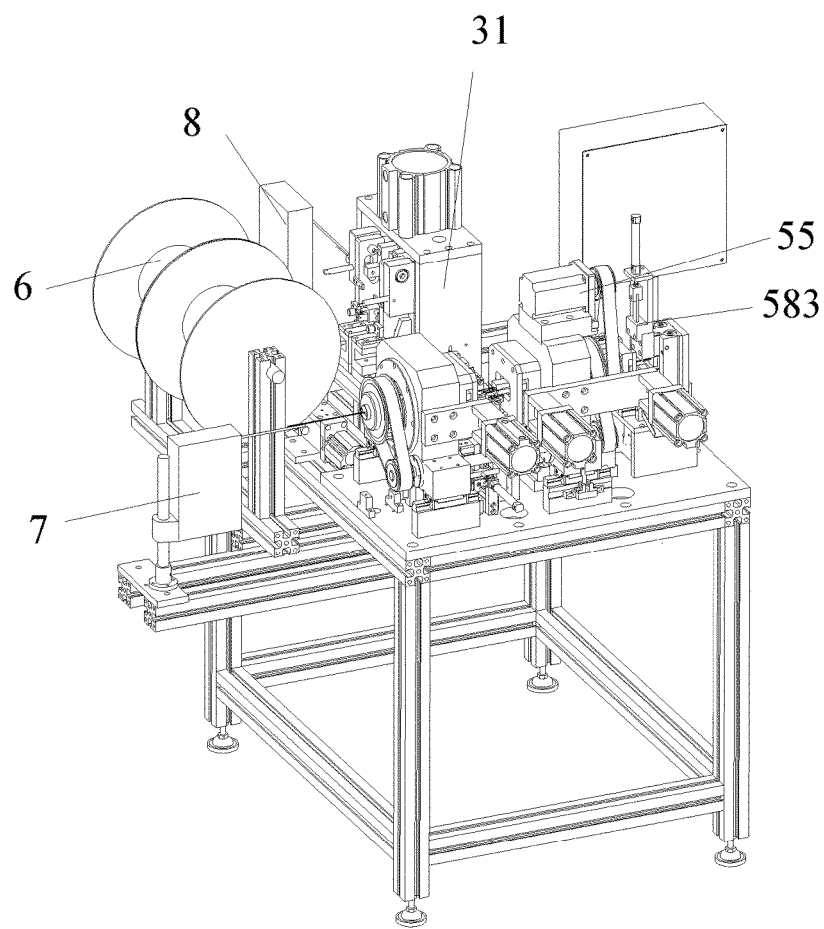
FIG. 3 is a perspective schematic view showing the structure of the preferred embodiment of an electric heating wire winding device according to the present application.
Figure 4:
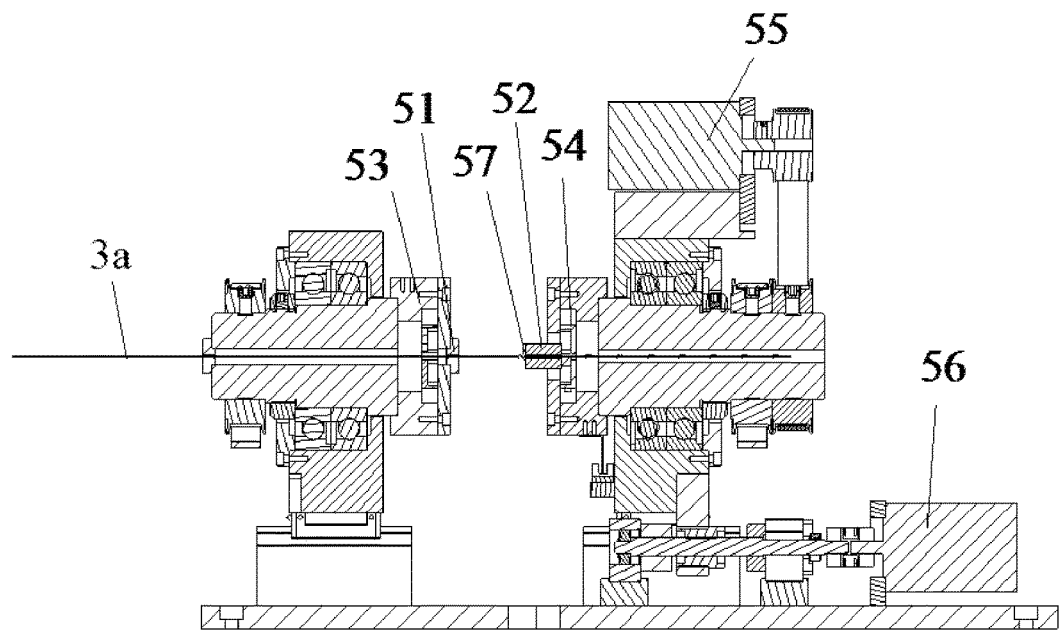
FIG. 4 is a sectional schematic view showing the structure of the preferred embodiment of a wire winding assembly in the electric heating wire winding device according to the present application.

For making objects, features and advantages of the present application more apparent and easier to be understood, the technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application FIG. 1 is a schematic view showing the structure of a preferred embodiment of an electric heating wire winding device according to the present application. FIG. 2 is a sectional view showing the structure of the preferred embodiment of an electric heating wire winding device according to the present application. FIG. 3 is a perspective view showing the structure of the preferred embodiment of an electric heating wire winding device according to the present application. FIG. 4 is a sectional view showing the structure of the preferred embodiment of a wire winding assembly of an electric heating wire winding device according to the present application. The structure of the electric heating wire winding device is described in details in conjunction with the above drawings.

An electric heating wire winding device in the embodiment of the present application includes a connection assembly 3, a delivering assembly 4, and a wire winding assembly 5.

The connection assembly 3 is configured to connect an electronic wire 1a having a first preset length to an electric heating wire 2a in a delivering path. The electric heating wire 2a includes at least two heating sections 21a for atomizing tobacco liquid and at least one connection section 22a for connecting a power source of an electronic cigarette. The heating sections 21a are spaced apart and are connected by the connection section 22a. The electronic wire 1a having the first preset length is connected to the connection section 22a of the electric heating wire 2a.

The delivering assembly 4 is connected to the connection assembly 3 such that the electric heating wire 2a connected to the electronic wire 1a having the first preset length is delivered to the wire winding assembly 5.

The wire winding assembly 5 includes a first clamping component 51, a second clamping component 52, a first rotating component 53, a second rotating component 54, a first power device 55, a second power device 56, and a third clamping component 57.

The first clamping component 51 and the second clamping component 52 are oppositely arranged for respectively clamping two ends of a liquid guiding rope 3a. The first rotating component 53 is connected to the first clamping component 51, the second rotating component 54 is connected to the second clamping component 52, the first power device 55 is connected to the first rotating component 53 and the second rotating component 54 for driving the first rotating component 53 and the second rotating component 54, and the second power device 56 is connected to the second clamping component 52 for driving the second clamping component 52.

The third clamping component 57, which is arranged on the second clamping component 52 and faces to the first clamping component 51, is configured to clamp the electronic wire 1a with the first preset length connected to a free end of the electric heating wire 2a.

The first power device 55 is configured to rotate the first rotating component 53 and the second rotating component 54, and the second power device 56 is configured to allow the second clamping component 52 to axially move along the liquid guiding rope 3a.

In the case that the electronic wire 1a with the first preset length connected to the free end of the electric heating wire 2a rotates together with the liquid guiding rope 3a and moves in an axial direction of the liquid guiding rope 3a away from the first clamping component 51, the electric heating wire 2a is winded around the liquid guiding rope 3a.

It should be noted that, the electric heating wire 2a includes at least two heating sections 21a for atomizing the tobacco liquid and at least one connection section 22a for connecting to the power source of electronic cigarette, and the heating sections 21a and the connection section 22a are a section of electric heating wire 2a. The first clamping component 51 and the second clamping component 52 are oppositely arranged for respectively clamping two ends of the liquid guiding rope 3a. That is, the first clamping component 51 and the second clamping component 52 are respectively located at the two ends of the liquid guiding rope 3a. The liquid guiding rope 3a may be a glass-fiber wire, the materials of which are not limited herein.

In the embodiment of the present application, the third clamping component 57, which is arranged on the second clamping component 52 and faces to the first clamping component 51, is configured to clamp the electronic wire 1a with the first preset length connected to the free end of the electric heating wire 2a. The first power device 55 is configured to rotate the first rotating component 53 and the second rotating component 54, and the second power device 56 is configured to allow the second clamping component 52 to move in the axial direction of the liquid guiding rope 3a. In the case that the electronic wire 1a with the first preset length connected to the free end of the electric heating wire 2a rotates together with the liquid guiding rope 3a and they are moved in an axial direction of the liquid guiding rope 3a away from the first clamping component 51, the electric heating wire 2a is winded around the liquid guiding rope 3a. Therefore, the wire winding device according to the present application not only can improve the working efficiency, but also can accurately control a length of the winded electric heating wire, which ensures the quality and service life of electronic cigarette products.

Further, as shown in FIG. 1, the wire winding component 5 further includes a cutting component, which includes a first cutting component 581, a second cutting component 582, and a third cutting component 583.

The first cutting component 581 and the second cutting component 582 are both arranged on the second clamping component 52 at one end close to the first clamping component 51. The third cutting component 583 is arranged on the second clamping component 52 at one end away from the first clamping component 51.

The first cutting component 581 is configured to cut off the electric heating wire 2a at the end away from the third clamping component 57 of the electronic wire 1a with the first preset length, after the electronic wire 1a with the first preset length and connected to the free end of the electronic wire 1a is clamped by the third clamping component 57.

The second cutting component 582 is configured to cut off the electric heating wire 2a at the end away from the third clamping component 57 of another electronic wire 1a with the first preset length adjacent to the last electronic wire 1a with the first preset length after the last electric heating wire 2a is winded around the liquid guiding rope 3a.

The third cutting component 583 is configured to cut off the liquid guiding rope 3a after the liquid guiding rope 3a winded with the electric heating wire 2a is delivered to the third cutting component 583, thus the liquid guiding rope 3a with a second preset length is obtained.

Figure 5:
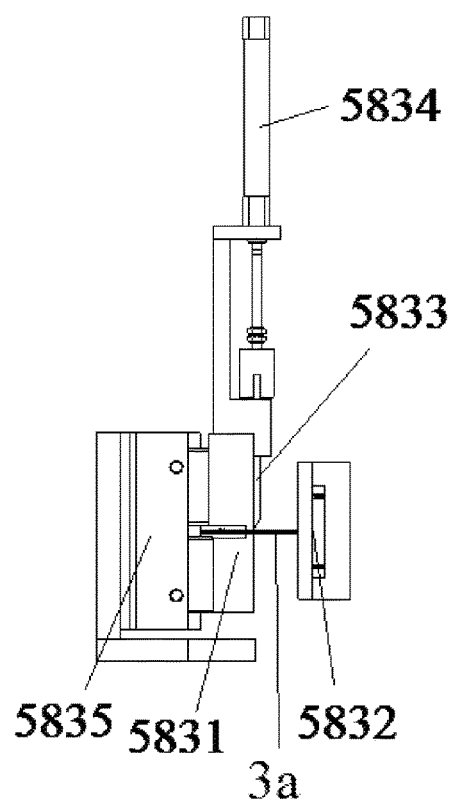
FIG. 5 is a sectional schematic view showing the structure of the preferred embodiment of a third cutting component in the electric heating wire winding device according to the present application.

Specifically, as shown in FIG. 5, the third cutting component 583 is provided with a fourth clamping component 5831, a fifth clamping component 5832, a cutting tool 5833, a first air cylinder 5834, a second air cylinder 5835 and a third air cylinder.

The fourth clamping component 5831 and the fifth clamping component 5832 are oppositely arranged for respectively clamping two ends of the liquid guiding rope 3a winded with the electric heating wire 2a.

The cutting tool 5833 is arranged on an end surface of the fourth clamping component 5831.

The first air cylinder 5834 is connected to the cutting tool 5833 such that the cutting tool 5883 can be pushed to cut off the liquid guiding rope 3a.

The second air cylinder 5835 is connected to the fourth clamping component 5831 such that the fourth clamping component 5831 can clamp or loosen the liquid guiding rope 3a.

The third air cylinder is connected to the fifth clamping component 5832 such that the fifth clamping component 5832 can clamp or loosen the liquid guiding rope 3a.

It should be noted that, the fourth clamping component 5831 and the fifth clamping component 5832 are oppositely arranged for respectively clamping the two ends of the liquid guiding rope 3a winded with the electric heating wire 2a. That is, the fourth clamping component 5831 and the fifth clamping component 5832 are respectively arranged at the two ends of the liquid guiding rope 3a winded with the electric heating wire 2a.

Figure 6:
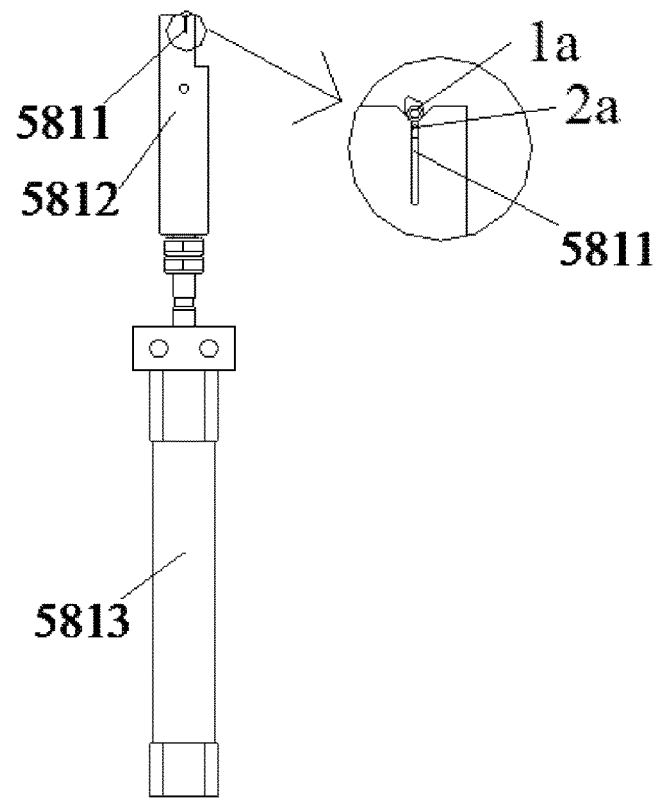
FIG. 6 is a sectional schematic view showing the structure of the preferred embodiment of a first cutting component in the electric heating wire winding device according to the present application.

More specifically, as shown in FIG. 6, the first cutting component 581 is provided with a cutting tool 5811, a fixing block 5812 and a fourth air cylinder 5813.

The fixing block 5812 has one end connected to the cutting tool 5811 for fixing the cutting tool 5811.

The fourth air cylinder 5813 is connected at another end of the fixing block 5812 for pushing the fixing block 5812 and thus allowing the cutting tool 5811 to cut off the electric heating wire 2a at one end away from the third clamping component 57 of the electronic wire 1a with the first preset length.

More specifically, the fixing block 5812 is provided with a funnel-shaped port.

The funnel-shape port is located on an end portion of the fixing block 5812 in contact with the electric heating wire 2a, such that the electronic wire 1a with the first preset length having a larger diameter compared with the electric heating wire 2a can be clamped by the funnel-shaped port so as to be not in contact with the cutting tool 5811, and the electric heating wire 2a having a smaller diameter compared with the electronic wire 1a with the first preset length can fall into the funnel-shaped port so as to be cut off by the cutting tool 5811.

It should be noted that, the second cutting component 582 has a same structure with the first cutting component 581, and since the specific structure of the first cutting component 581 is described in details hereinbefore, the structure of the first component 581 is not described in details hereinafter.

Figure 7:
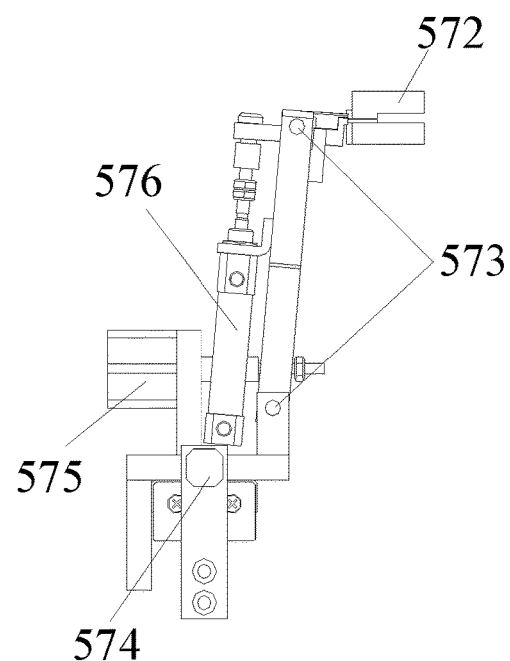
FIG. 7 is a sectional schematic view showing the structure of the preferred embodiment of a third clamping component in the electric heating wire winding device according to the present application.

More specifically, as shown in FIG. 7, the third clamping component 57 is provided with a mechanical hand, a clamping piece 572, a connecting shaft 573, a fifth air cylinder 574, a sixth air cylinder 575 and a seventh air cylinder 576.

The mechanical hand is configured to deliver the electric heating wire connected to the electronic wire with the first preset length to the clamping piece 572.

The clamping piece 572 is rotatably connected to the connecting shaft 573.

The fifth air cylinder 574 is connected to the mechanical hand for moving the mechanism hand transversely.

The sixth air cylinder 575 is connected to the mechanical hand for moving the mechanism hand longitudinally.

The seventh air cylinder 576 is connected to the mechanical hand for clamping or loosening the mechanism hand.

Figure 8:
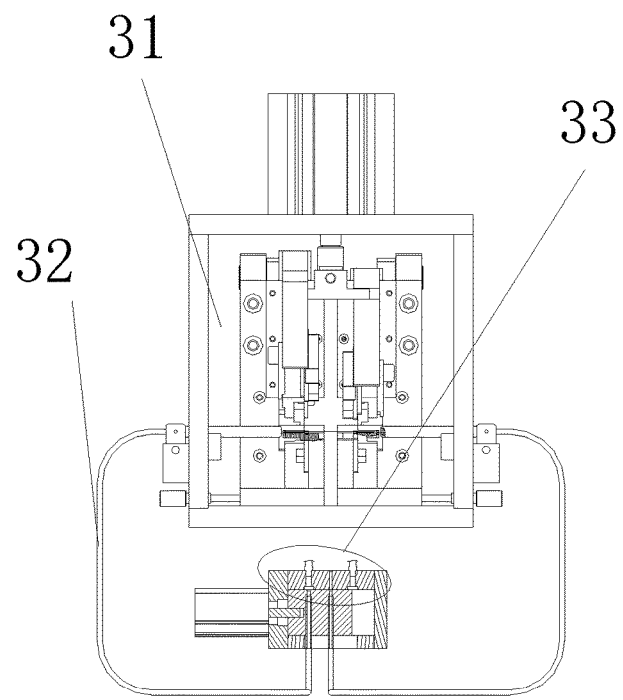
FIG. 8 is a sectional schematic view showing the structure of the preferred embodiment of a connection assembly in the electric heating wire winding device according to the present application.

Further, as shown in FIG. 8, the connection assembly 3 is provided with a riveting machine 31, a wire sending pipe 32 and an airflow source 32.

The riveting machine 31 is configured to rivet the electric heating wire and the electronic wire with the first preset length.

One end of the wire sending pipe 32 is fixedly arranged at a riveting portion of the riveting machine 31 for delivering the electronic wire with the first preset length to the riveting portion of the riveting machine 31.

The airflow source 33 is arranged at another end of the wire sending pipe 32 for blowing the electronic wire with the first preset length to the riveting portion of the riveting machine 31 from the wire sending pipe 32.

Further, as shown in FIG. 3, the electric heating wire winding device is fixedly provided with a roller 6 for delivering a connecting terminal, which is used for connecting the electric heating wire and the electronic wire with the first preset length, to the connection assembly 3.

Further, as shown in FIGS. 1 and 3, the electric heating wire winding device further includes a first tension device 7 and a second tension device 8.

The first tension device 7 is fixedly arranged at one end of the liquid guiding rope 3a and is connected to the liquid guiding rope 3a so as to control the tension of the liquid guiding rope 3a.

The second tension device 8 is fixedly arranged at one end of the electric heating wire 2a and is connected to the electric heating wire 2a so as to control the tension of the electric heating wire 2a.

Figure 9:
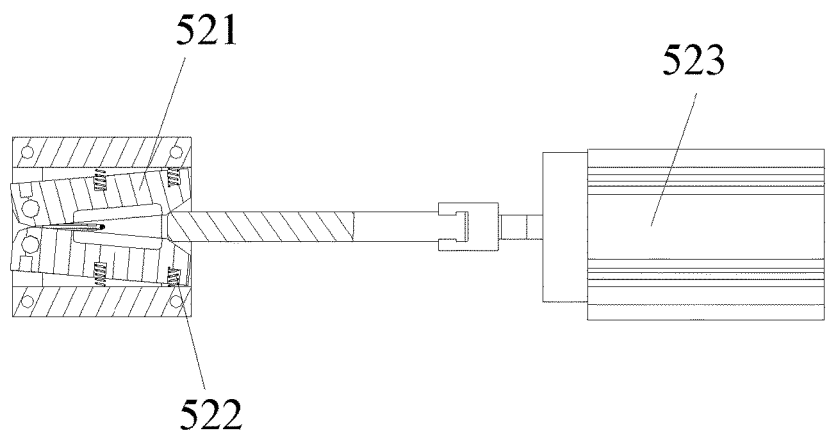
FIG. 9 is a sectional schematic view showing the structure of the preferred embodiment of a second clamping component in the electric heating wire winding device according to the present application.

More specifically, as shown in FIG. 9, the second clamping component 52 is provided with a clamping piece 521, multiple springs 522, and an eighth air cylinder 523.

The clamping piece 521 is configured to clamp a free end of the liquid guiding rope.

The eighth air cylinder 523 is connected to the clamping piece 521 for loosening the clamping piece 521 in the case that the second power device 56 moves the second clamping component 52 in the axial direction of the liquid guiding rope, thus allowing the liquid guiding rope to be in a loosened state.

The springs 522 are connected to the clamping piece 521 for clamping the liquid guiding rope through an elastic potential energy of the springs 522 in the case that the eighth air cylinder 523 returns to an initial state.

For better implementing the electric heating wire winding device in the embodiment according to the present application, a method for manufacturing an electric heating wire element using the electric heating wire winding device is provided hereinafter.

Figure 10:
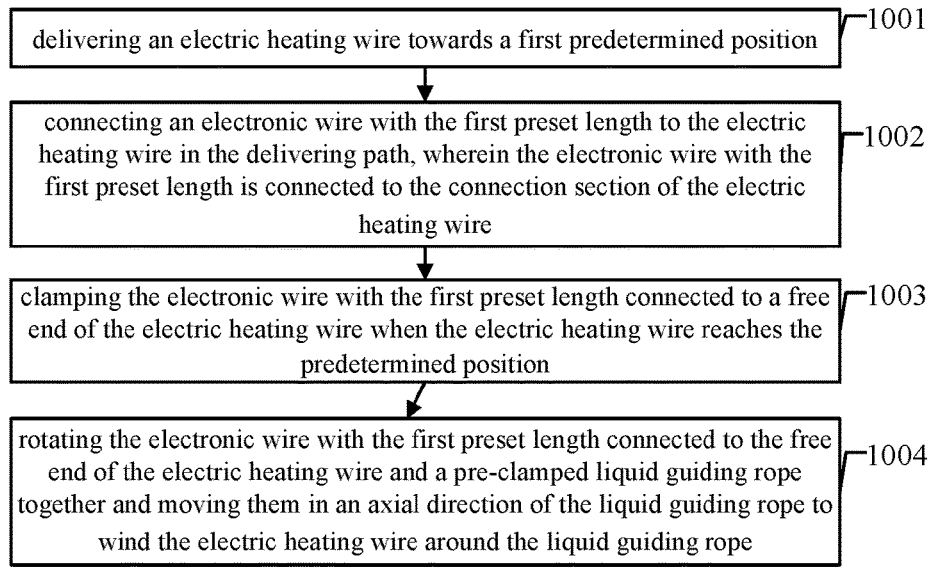
FIG. 10 is a flow chart schematic view showing a method for manufacturing an electric heating wire element according to the present application.

Referring to FIG. 10, one embodiment of the method for manufacturing the electric heating wire element 4a according to the present application includes step 1001 to step 1004.

Step 1001 includes delivering an electric heating wire towards a first predetermined position.

It should be noted that the electric heating wire includes at least two heating sections for atomizing tobacco liquid and at least one connection section for connecting a power source for electronic cigarette. The heating sections are spaced apart and are connected via the connection section, and the heating sections and the connection section are a section of electric heating wire.

Step 1002 includes connecting at least one electronic wire with a first preset length to the electric heating wire located at the delivering path, wherein the electronic wire with the first preset length is connected to the connection section of the electric heating wire.

Step 1003 includes clamping the electronic wire with the first preset length connected to a free end of the electric heating wire, when the electric heating wire reaches the predetermined position.

Step 1004 includes rotating the electronic wire with the first preset length connected to the free end of the electric heating wire and the pre-clamped liquid guiding rope together and moving them in an axial direction of the liquid guiding rope, thus the electric heating wire is winded around the liquid guiding rope.

In the embodiment of the present application, the electric heating wire is winded around the liquid guiding rope by rotating the electronic wire with the first preset length connected to the free end of the electric heating wire and the pre-clamped liquid guiding rope to together and moving them in the axial direction of the liquid guiding rope. Therefore, the wire winding device according to the present application can not only improve the working efficiency, but also accurately control a length of the winded electric heating wire, which ensures the quality and the service life of electronic cigarette products.

Figure 11:
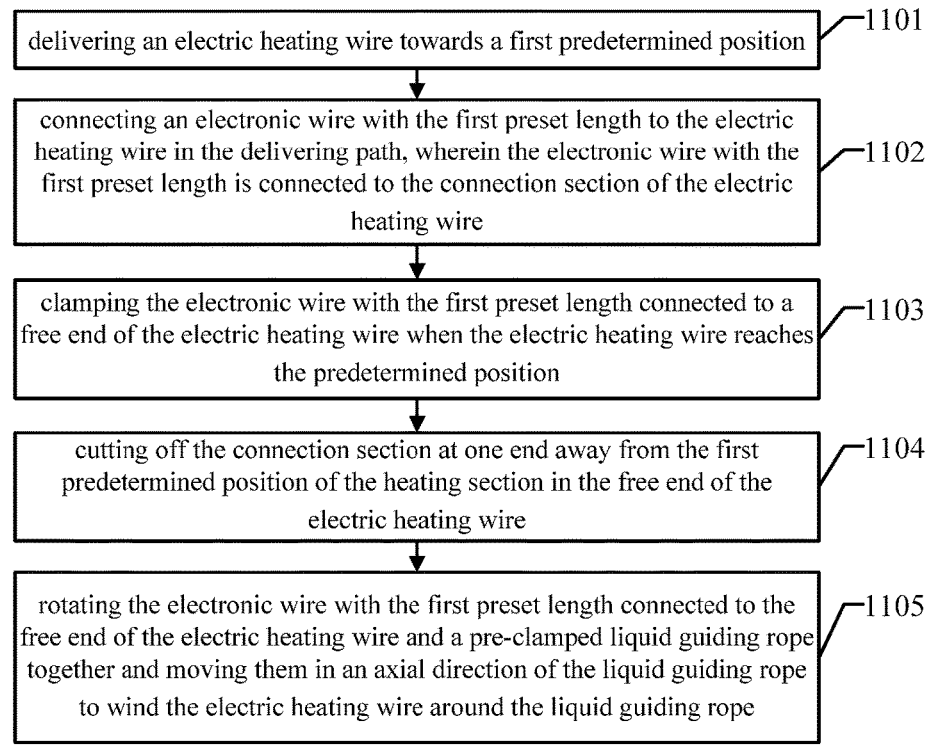
FIG. 11 is another flow chart schematic view showing the method for manufacturing the electric heating wire element according to the present application.

Referring to FIG. 11, another embodiment of the method for manufacturing the electric heating wire element according to the present application includes step 1101 to step 1105.

Step 1101 includes delivering an electric heating wire towards a first predetermined position.

It should be noted that, the electric heating wire includes at least two heating sections to atomize tobacco liquid and at least one connection section for connecting a power source of electronic cigarette. The heating sections are spaced apart and are connected via the connection section, and the heating sections and the connection section are a section of electric heating wire.

Step 1102 includes connecting at least one electronic wire with the first preset length to the electric heating wire in the delivering path, wherein the electronic wire with the first preset length is connected to the connection section of the electric heating wire.

Step 1103 includes clamping the electronic wire with the first preset length connected to a free end of the electric heating wire when the electric heating wire reaches the predetermined position.

Step 1104 includes cutting off the connection section at one end away from the first predetermined position of the heating section in the free end of the electric heating wire.

Step 1105 includes rotating the electronic wire with the first preset length connected to the free end of the electric heating wire and a pre-clamped liquid guiding rope to rotate together and moving them in an axial direction of the liquid guiding rope, thus, the electric heating wire is winded around the liquid guiding rope.

In this embodiment, the electric heating wire is winded around the liquid guiding rope by cutting off the connection section at one end away from the first predetermined position of the heating section in the free end of the electric heating wire.

Figure 12:
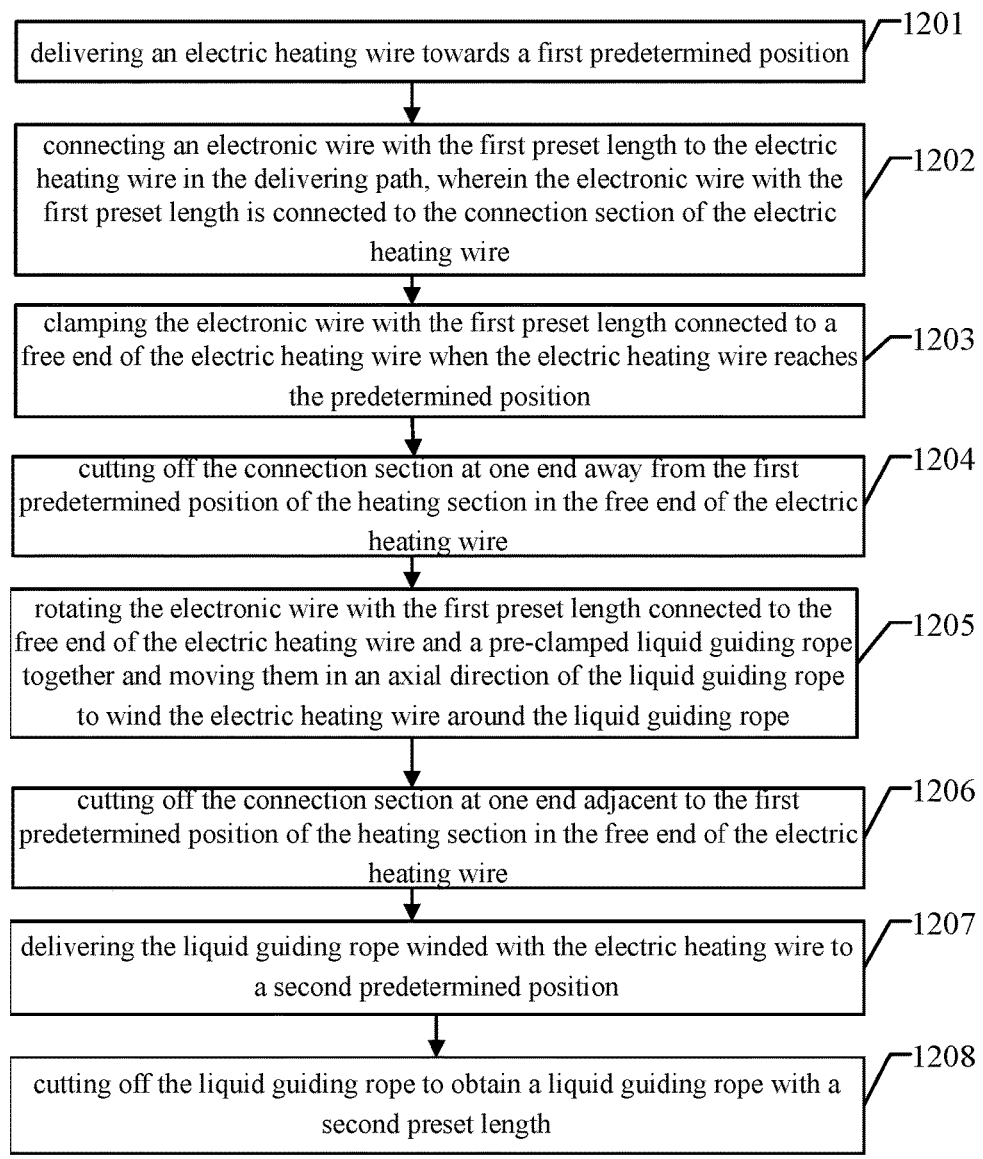
FIG. 12 is another flow chart schematic view showing the method for manufacturing the electric heating wire element according to the present application.

Referring to FIG. 12, another embodiment of the method for manufacturing the electric heating wire element according to the present application includes step 1201 to step 1208.

Step 1201 includes delivering an electric heating wire towards a first predetermined position.

It should be noted that, the electric heating wire includes at least two heating sections for atomizing tobacco liquid and at least one connection section for connecting a power source of the electronic cigarette. The heating sections are spaced apart and are connected via the connection section, and the heating sections and the connection section are a section of electric heating wire.

Step 1202 includes connecting an electronic wire with the first preset length to the electric heating wire in the delivering path, wherein the electronic wire with the first preset length are connected to the connection section of the electric heating wire.

Step 1203 includes clamping the electronic wire with the first preset length connected to a free end of the electric heating wire in the case that the electric heating wire reaches the predetermined position.

Step 1204 includes cutting off the connection section at one end away from the first predetermined position of the heating section in the free end of the electric heating wire.

Step 1205 includes rotating the electronic wire with the first preset length connected to the free end of the electric heating wire and a pre-clamped liquid guiding rope together and moving them in an axial direction of the liquid guiding rope, thus, the electric heating wire is winded around the liquid guiding rope.

Step 1206 includes cutting off the connection section at one end adjacent to the first predetermined position of the heating section in the free end of the electric heating wire.

Step 1207 includes delivering the liquid guiding rope winded with the electric heating wire to a second predetermined position.

Step 1208 includes cutting off the liquid guiding rope to obtain a liquid guiding rope with a second preset length.

In this embodiment, after the electric heating wire is winded around the liquid guiding rope, the liquid guiding rope of the second preset length is obtained by cutting off the connection section at one end adjacent to the first predetermined position of the heating section in the free end of the electric heating wire and delivering the liquid guiding rope winded with the electric heating wire to a second predetermined position and cutting off the liquid guiding rope.

Figure 13:
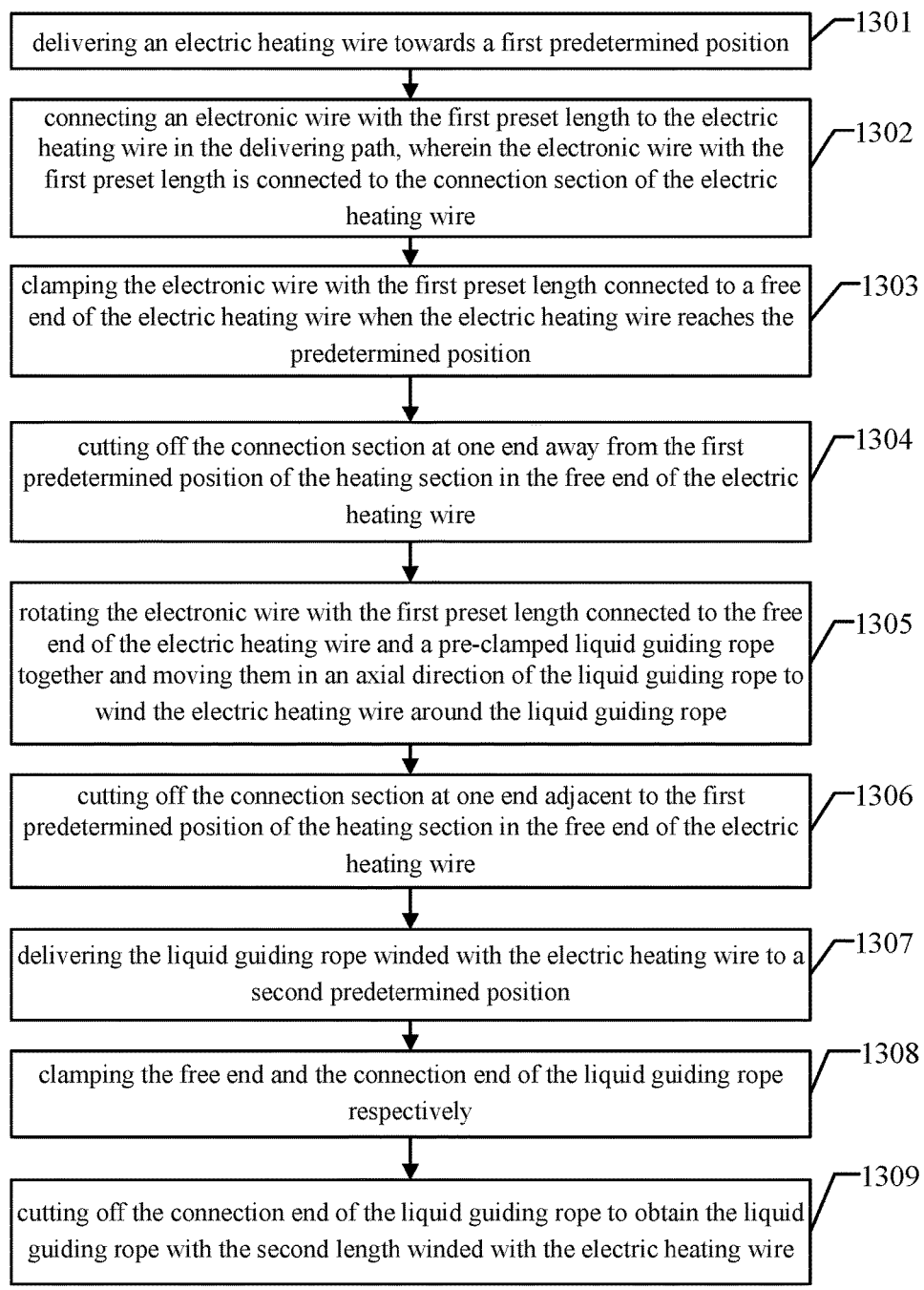
FIG. 13 is another flow chart schematic view showing the method for manufacturing the electric heating wire element according to the present application.

Referring to FIG. 13, another embodiment of the method for manufacturing the electric heating wire element according to the present application includes step 1301 to step 1309.

Step 1301 includes delivering an electric heating wire towards a first predetermined position.

It should be noted that, the electric heating wire includes at least two heating sections for atomizing tobacco liquid and at least one connection section for connecting a power source of an electronic cigarette. The heating sections are spaced apart and are connected via the connection section, and the heating sections and the connection section are a section of electric heating wire.

Step 1302 includes connecting at least one electronic wire with a first preset length to the electric heating wire in the delivering path, wherein the electronic wire with the first preset length is connected to the connection section of the electric heating wire.

Step 1303 includes clamping the electronic wire with the first preset length connected to a free end of the electric heating wire when the electric heating wire reaches the predetermined position.

Step 1304 includes cutting off the connection section at one end away from the first predetermined position of the heating section in the free end of the electric heating wire.

Step 1305 includes rotating the electronic wire with the first preset length connected to the free end of the electric heating wire and a pre-clamped liquid guiding rope to rotate together and moving them in an axial direction of the liquid guiding rope, thus the electric heating wire is winded around the liquid guiding rope.

Step 1306 includes cutting off the connection section at one end adjacent to the first predetermined position of the heating section in the free end of the electric heating wire.

Step 1307 includes delivering the liquid guiding rope winded with the electric heating wire to a second predetermined position.

Step 1308 includes clamping the free end and the connection end of the liquid guiding rope respectively.

Step 1309 includes cutting off the connection end of the liquid guiding rope, thus the liquid guiding rope with the second preset length winded with the electric heating wire is obtained.

In this embodiment, the liquid guiding rope with the second preset length winded with the electric heating wire is obtained by clamping the free end and the connection end of the liquid guiding rope respectively and cutting off the connection end of the liquid guiding rope.

The above embodiments are only intended for describing the technical solutions of the present application, and should not be interpreted as limitation to the present application. Although the present application is described in detail in conjunction with the above embodiments, it should be understood that, for those skilled in the art, modifications may be made to the technical solutions of the above embodiments, or equivalent substitutions may be made to part of the technical features in the technical solutions; and theses modifications and substitutions also fall into the scope of the present application defined by the claims.

The invention claimed is:

1. A method for manufacturing an electric heating wire element, wherein the electric heating wire element comprises a liquid guiding rope and the electric heating wire winded around the liquid guiding rope, and the method comprises:
    delivering the electric heating wire towards a first predetermined position, wherein the electric heating wire comprises at least two heating sections for atomizing tobacco liquid and at least one connection section for connecting a power source of an electronic cigarette, and the at least two heating sections are spaced apart and are connected via the at least one connection section;
    connecting an electronic wire with a first preset length to the electric heating wire in a delivering path, wherein the electronic wire with the first preset length is connected to the at least one connection section of the electric heating wire;
    clamping the electronic wire with the first preset length connected to a free end of the electric heating wire when the electric heating wire reaches the predetermined position; and
    rotating the electronic wire with the first preset length connected to the free end of the electric heating wire and the liquid guiding rope that is pre-clamped, together, and moving the electronic wire and the liquid guiding rope in an axial direction of the liquid guiding rope to wind the electric heating wire around the liquid guiding rope.

2. The method for manufacturing the electric heating wire element according to claim 1, wherein after clamping the electronic wire with the first preset length connected to a free end of the electric heating wire, the method further comprises:
    cutting off the at least one connection section of the electric heating wire at one end away from the first predetermined position of the heating section in the free end of the electric heating wire.

3. The method for manufacturing the electric heating wire element according to claim 1, wherein following the step of winding the electric heating wire around the liquid guiding rope, the method further comprises:
    cutting off the at least one connection section of the electric heating wire at one end adjacent to the first predetermined position of the at least two heating sections in the free end of the electric heating wire;
    delivering the liquid guiding rope winded with the electric heating wire to a second predetermined position; and
    cutting off the liquid guiding rope to form the liquid guiding rope with a second preset length.

4. The method for manufacturing the electric heating wire element according to claim 2, wherein following winding the electric heating wire around the liquid guiding rope, the method further comprises:
    cutting off the at least one connection section of the electric heating wire at one end adjacent to the first predetermined position of the at least two heating sections in the free end of the electric heating wire;
    delivering the liquid guiding rope winded with the electric heating wire to a second predetermined position; and
    cutting off the liquid guiding rope to form the liquid guiding rope with a second preset length.

5. The method for manufacturing the electric heating wire element according to claim 3, wherein the step of cutting off the liquid guiding rope further comprises:
    clamping the free end of the electric heating wire and a connection end of the liquid guiding rope respectively; and
    cutting off the connection end of the liquid guiding rope to obtain the liquid guiding rope with a second length winded with the electric heating wire.

6. The method for manufacturing the electric heating wire element according to claim 4, wherein the step of cutting off the liquid guiding rope further comprises:
    clamping the free end of the electric heating wire and a connection end of the liquid guiding rope respectively; and
    cutting off the connection end of the liquid guiding rope to obtain the liquid guiding rope with a second length winded with the electric heating wire.

* * * * *